United States Patent
Henke et al.

(10) Patent No.: US 11,690,799 B2
(45) Date of Patent: Jul. 4, 2023

(54) MICRONEEDLE SYSTEM FOR APPLYING INTERFERON

(71) Applicant: LTS LOHMANN THERAPIE-SYSTEME AG, Andernach (DE)

(72) Inventors: Stefan Henke, Kirchen (DE); Andreas Henning, Koblenz (DE); Rolf Pracht, Höhr-Grenzhausen (DE); Danny Brodkorb, Koblenz (DE); Sebastian Scherr, Neuhäusel (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 263 days.

(21) Appl. No.: 17/048,773

(22) PCT Filed: Apr. 23, 2019

(86) PCT No.: PCT/EP2019/060396
§ 371 (c)(1),
(2) Date: Oct. 19, 2020

(87) PCT Pub. No.: WO2019/202170
PCT Pub. Date: Oct. 24, 2019

(65) Prior Publication Data
US 2021/0220261 A1  Jul. 22, 2021

(30) Foreign Application Priority Data

Apr. 19, 2018  (DE) .................... 10 2018 109 406.4
Jun. 21, 2018  (DE) .................... 10 2018 114 930.1

(51) Int. Cl.
*A61M 37/00*  (2006.01)
*A61K 9/00*  (2006.01)
(Continued)

(52) U.S. Cl.
CPC ............ *A61K 9/0021* (2013.01); *A61K 38/21* (2013.01); *A61K 47/10* (2013.01); *A61K 47/26* (2013.01);
(Continued)

(58) Field of Classification Search
CPC ...... A61K 9/0021; A61K 38/21; A61K 47/10; A61K 47/26; A61K 47/32; A61M 37/0015; A61M 2037/0023; A61M 2037/0061
See application file for complete search history.

(56) References Cited

U.S. PATENT DOCUMENTS

2007/0081977 A1    4/2007  Horstmann
2011/0190688 A1*   8/2011  Tagliaferri ......... A61K 31/4468
                                                          604/20
(Continued)

FOREIGN PATENT DOCUMENTS

CN   104069484 A   10/2014
DE   10353629 A1    6/2005
(Continued)

OTHER PUBLICATIONS

Chen, J., et al., "Dissolving microneedle-based intradermal delivery of interferon-α-2b", Drug Development and Industrial Pharmacy, vol. 42, No. 6, (2015), pp. 1-7.
(Continued)

*Primary Examiner* — Amber R Stiles
(74) *Attorney, Agent, or Firm* — Faegre Drinker Biddle & Reath LLP

(57) ABSTRACT

The present invention relates to a microneedle system (MNS) for the intradermal delivery of interferon, wherein polyvinylpyrrolidone is the major constituent of a completely soluble formulation.

21 Claims, 2 Drawing Sheets

Figure 1:
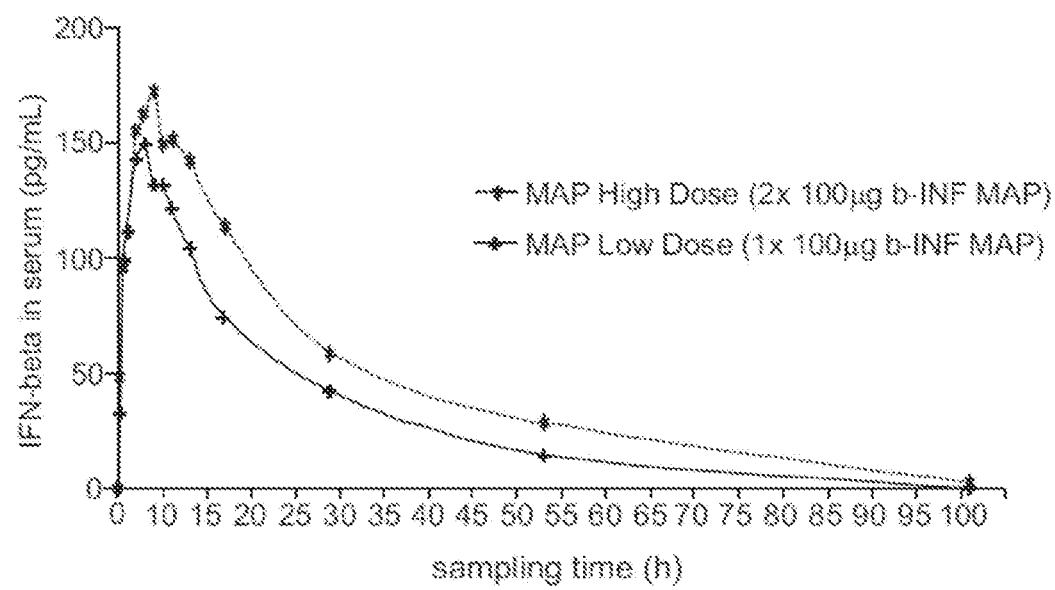

(51) Int. Cl.
*A61K 38/21* (2006.01)
*A61K 47/32* (2006.01)
*A61K 47/26* (2006.01)
*A61K 47/10* (2017.01)

(52) U.S. Cl.
CPC ......... *A61K 47/32* (2013.01); *A61M 37/0015* (2013.01); *A61M 2037/0023* (2013.01)

(56) References Cited

U.S. PATENT DOCUMENTS

| | | | |
|---|---|---|---|
| 2013/0041330 A1 | 2/2013 | Matsudo et al. | |
| 2013/0123707 A1* | 5/2013 | Determan | A61K 47/32 604/173 |
| 2014/0371713 A1 | 12/2014 | Quan et al. | |
| 2015/0216796 A1* | 8/2015 | Ishibashi | A61K 9/0021 604/46 |
| 2015/0283252 A1 | 10/2015 | Vadgama et al. | |
| 2016/0015952 A1 | 1/2016 | Omachi et al. | |
| 2017/0252546 A1 | 9/2017 | Park et al. | |
| 2017/0266427 A1 | 9/2017 | Nishimura et al. | |
| 2017/0296465 A1 | 10/2017 | Yoshida et al. | |
| 2018/0001070 A1 | 1/2018 | Kaspar et al. | |
| 2018/0243543 A1 | 8/2018 | Baek et al. | |

FOREIGN PATENT DOCUMENTS

| | | |
|---|---|---|
| EP | 0270799 A1 | 6/1988 |
| EP | 2540337 A1 | 1/2013 |
| EP | 2815784 A1 | 12/2014 |
| EP | 2891506 A1 | 7/2015 |
| JP | 63-179833 A | 7/1988 |
| JP | 2004-529917 A | 9/2004 |
| JP | 2010-510978 A | 4/2010 |
| JP | 2017-528434 A | 9/2017 |
| JP | 2018-039761 A | 3/2018 |
| KR | 10-1776659 B1 | 9/2017 |
| RU | 2508135 C2 | 2/2014 |
| WO | 02/80976 A2 | 10/2002 |
| WO | WO-2007030477 A2 | 3/2007 |
| WO | 2008/062481 A2 | 5/2008 |
| WO | 2010/087300 A1 | 8/2010 |
| WO | 2012/153266 A2 | 11/2012 |
| WO | 2016/013755 A1 | 1/2016 |
| WO | 2016/142705 A1 | 9/2016 |
| WO | 2018/047800 A1 | 3/2018 |

OTHER PUBLICATIONS

International Preliminary Examination Report for PCT/EP2019/060396 dated Jul. 15, 2020.
International Search Report for PCT/EP2019/060396 dated Jul. 25, 2019.
Written Opinion of the International Searching Authority for PCT/EP2019/060396 dated Jul. 25, 2019.
Min Wang et al., "Recent advances in the design of polymeric microneedles for transdermal drug delivery and biosensing", Lab on a Chip, vol. 17, No. 8, Jan. 1, 2017, pp. 1373-1387.

* cited by examiner

MICRONEEDLE SYSTEM FOR APPLYING INTERFERON

CROSS-REFERENCE TO RELATED APPLICATIONS

This application is a national stage application (under 35 U.S.C. § 371) of PCT/EP2019/060396, filed Apr. 23, 2019, which claims benefit of German Application No. 10 2018 114 930.1, filed Jun. 21, 2018 and German Application No. 10 2018 109 460.4, filed Apr. 19, 2018, all of which are incorporated herein by reference in their entirety.

The present invention relates to a microneedle system (for short: MNS) for the intradermal delivery of interferon.

Interferons are endogenous messengers by way of which different cells of the immune system communicate with one another. Interferon beta-1a is produced by genetic engineering and differs only slightly from human beta interferon. The active ingredient is used for relapsing-remitting and secondary progressive forms of multiple sclerosis (MS). It is suspected that the use of beta interferon inhibits the activity of autoreactive T cells (defense cells directed against endogenous tissue), thereby delaying damage to the myelin substance, which surrounds and protects nerve fibers.

Beta interferon products presently used in the treatment of MS (such as Avonex®, Rebit®) are injected intramuscularly or subcutaneously several times a week. As a result of the self-medication of MS patients, along with the associated risks of infections and pinprick injuries, patient compliance can be significantly improved during the beta interferon therapy when a dissolving microarray is used. According to the expert opinion, a further advantage of the intradermal delivery of beta interferon may be that the active ingredient is directly released in the vicinity of immunocompetent target cells in the upper layers of the skin, which, in turn, in contrast to the parenteral delivery of the active ingredient (for example in the form of a SC infection), could result in a reduction in the frequently occurring undesirable side effects (flu-like symptoms, increase in certain liver values).

The skin consists of several layers. The outermost layer of the skin, this being the *Stratum corneum*, has known blocking properties to prevent foreign substances from penetrating into the body and the body's own substances from exiting the body. The *stratum corneum*, which is a complex structure composed of compacted horny cell residues having a thickness of approximately 10 to 30 micrometers, forms a watertight membrane for this purpose to protect the body. The natural impermeability of the *stratum corneum* prevents most pharmaceutical active ingredients and other substances from being administered through the skin barrier as part of a transdermal delivery form. Langerhans cells are found throughout the basal granular layer of the epithelium and play an important role in the initial defense of the immune system against penetrating organisms.

Microneedle systems (MNS), which are composed of a microneedle array (MNA) and possibly further components, can use a pressure force to press the microneedles (also referred to as skin penetration elements) of the array (MNA) against the delivery site on the skin so as to penetrate the *stratum corneum* and thereby establish a fluid channel so that interferon can be delivered transdermally. Such microneedle arrays (MA) in microneedle systems (MS) and the production thereof are described in the prior art and are also referred to as micro(needle)array patches.

It is likewise known in the prior art that proteins, including interferon, can be delivered via MNS (for example WO2007030477A2). WO2007030477A2 provides for the use of active ingredient particles, which are moved to the tip of a perforator by centrifugation.

It is therefore the object of the present invention to enable an intradermal delivery of interferon with the aid of an MNS, containing an MNA, based on a suitable formulation.

BRIEF DESCRIPTION OF THE FIGURES

FIG. 1 shows the active ingredient concentrations in the blood serum of the animals achieved after the delivery of the microarray.

FIG. 2 shows the points in time until the peak plasma level of beta interferon is reached for the intradermal delivery by way of a microarray patch compared to the SC injection.

FIG. 3 shows an antiviral beta interferon activity assay including Hep-2C cells and infectious EMCV according to Ph. Eur. 5.2.3.

FIG. 4 shows the storage stability of the beta interferon microarray, and more particularly the in-vitro beta interferon activity analysis after production, after 1 month, 3 months, and after 6 months, while being stored at room temperature (21° C.) and at refrigerator temperature (5° C.).

Surprisingly, polyvinylpyrrolidone (for short: PVP) is particularly well-suited for producing a completely soluble formulation for an MNA for the intradermal delivery of interferon.

The formulation according to the invention allows sufficient strength and complete solubility, so that sufficient stability can be achieved for interferon, even without stabilizers, for the use and dissolution of the MNA, and for the absorption and distribution of the active ingredient in the organism.

In addition to the suitability of the MNA for the direct intradermal use of interferon, the formulation according to the invention likewise relates to a stable storage of the formulation according to the invention for an interferon-containing microarray, in particular at room temperature, for 3 months and longer.

The formulation according to the invention was furthermore used within the scope of an in-vitro bioassay in a human cervical cancer model cell line. It was successfully demonstrated that lysis of the human cells does not occur, despite the addition of the encephalomyocarditis virus (EMCV). The interferon, embedded into the MNA, in the formulation according to the invention has a reliable antiviral effect and exhibits potency comparable to that of the original products. As a result, the same treatment success may be assumed as that achieved with an interferon injection (SC or IM), see FIGS. 1-4.

This object is thus achieved according to the invention by a microneedle array (MNA) according to claim 1, comprising a formulation including polyvinylpyrrolidone for use in the intradermal delivery of interferon, wherein polyvinylpyrrolidone is the major constituent of the formulation.

The invention therefore likewise relates to a microneedle system comprising an MNA for use in the intradermal delivery of interferon, wherein polyvinylpyrrolidone is the major constituent of the formulation.

The invention thus comprises a product including a microneedle array, comprising a formulation including polyvinylpyrrolidone for use in the intradermal delivery of interferon, wherein polyvinylpyrrolidone is the major constituent of the formulation.

Such a product is, for example, a pharmaceutical product comprising an above-described microneedle array (MNA)

for use in the intradermal delivery of interferon, and in particular for the treatment of multiple sclerosis (MS) or for interferon therapy.

A microneedle array according to the invention that has an interferon content of 0.1 μg to 200 μg, and in particular 10 μg to 100 μg per microneedle array, is particularly preferred.

According to the invention, the term "intradermal delivery" (synonym: "intracutaneous delivery") describes the administration of interferon from the MNA into the skin and requires the microneedles to penetrate the skin.

The term "interferon" comprises all, or one or more interferons (IFN), IFN alpha, beta, gamma, interferon tau, and in particular the interferons beta-1b, interferon beta-1a for treating multiple sclerosis (MS). Beta interferons are preferred according to the invention. Interferons are proteins or glycoproteins that exhibit an immunostimulating, and in particular an antiviral and antitumoral effect and represent endogenous cytokines.

The expression "wherein polyvinylpyrrolidone is the major constituent of the formulation" shall mean that, in addition to other adjuvants and the active ingredient interferon, polyvinylpyrrolidone is the major constituent in terms of quantity in % by weight, that is, polyvinylpyrrolidone accounts for the majority of % by weight in a composition of a completely soluble formulation.

The invention likewise relates to a method for carrying out an intradermal delivery of interferon, comprising the following steps:
  a) fixing a microneedle system according to the invention to the skin; and
  b) a microneedle array, comprising a completely soluble formulation including polyvinylpyrrolidone, penetrating the skin, wherein polyvinylpyrrolidone is the major constituent of the formulation.

Within the scope of the present invention, a microneedle system is a system comprising a device that causes the microneedle array for administering interferon onto the skin to be provided and to be intradermally delivered.

In a preferred embodiment, the microneedle system can comprise an applicator, such as a trigger device, which is electrically or mechanically controlled. For example, the applicator can comprise a plunger, which places or applies the microneedle array onto the skin, so that the microneedles penetrate the skin.

The trigger device can comprise a pump, a syringe or a spring, for example, whereby a push of the plunger can be carried out with sufficient energy. The plunger can be of any arbitrary shape and nature and is to primarily achieve that the microneedle array is provided from a first position into a second position for administering the interferon onto the skin. The applicator can furthermore comprise a push button or other trigger mechanisms.

The microneedle array can comprise a plurality of microneedles so as to be able to release interferon via the skin or into the skin of a patient, wherein the microneedle array is placed onto the skin of the patient. Each of the microneedles of the microneedle array preferably comprises an elongated shaft having two ends, the one end of the shaft forming the base of the microneedle by way of which the microneedle is attached to the planar carrier or by way of which the microneedle is integrated into the planar carrier. The end of the shaft located opposite the base preferably has a tapered shape so as to allow the microneedle to penetrate into the skin as easily as possible.

The microneedles can comprise a shaft having a round cross-section or a non-round cross-section, for example having a triangular, quadrangular or polygonal cross-section. The shaft can have one passage or multiple passages, extending from the needle base to the needle tip or approximately to the needle tip. The microneedles can be designed as (barbed) hooks, wherein one or more of these microneedles comprise one or more of such hooks. Furthermore, the microneedles can be configured in a helical shape and be rotatably disposed and thereby, when a rotating motion is applied, facilitate the penetration into the skin and effectuate anchoring in the skin (DE 103 53 629 A1), in particular at the desired penetration depth in the epidermis.

The diameter of a microneedle typically ranges between 1 μm and 1000 μm, and preferably between 10 μm and 100 μm. The length of a microneedle typically ranges between 5 μm and 6,000 μm, and in particular between 100 μm and 700 μm.

The microneedles are attached at the base thereof to a planar carrier or are integrated into a planar carrier. The microneedles are preferably disposed so as to be situated substantially perpendicularly to the surface area of the carrier. The microneedles can be arranged regularly or irregularly. An arrangement of multiple microneedles can comprise microneedles having differing cross-sectional shapes, differently dimensioned diameters and/or differing lengths. The arrangement made up of multiple microneedles can exclusively comprise hollow microneedles, for example.

The microneedle array can comprise a planar carrier, wherein the carrier essentially has a disk-shaped, plate-shaped or film-shaped basic shape. The carrier can have a round, an oval, a triangular, a quadrangular or a polygonal base surface area. The carrier can be produced from a variety of materials, such as a metal, a ceramic material, a semiconductor, an organic material, a polymer or a composite.

In a further preferred embodiment, the following substances, in addition to polyvinylpyrrolidone, are preferred in a formulation for producing the microneedles, which consist of or comprise these: disaccharide, preferably trehalose, non-ionic surfactants, preferably polysorbate (ethoxylated sorbitan fatty acid esters, such as Tween), polyalcohol, in particular glycerol (glycerin).

It is preferred that polyvinylpyrrolidone, as the major constituent, accounts for more than 35 wt. %, more than 45 wt. %, more than 55 wt. %, more than 65 wt. %, more than 75 wt. %, more than 85 wt. % in the formulation.

It is preferred that disaccharide, and in particular trehalose, as a minor constituent, accounts for more than 15 wt. %, more than 25 wt. %, more than 35 wt. % in the formulation.

TABLE 1

| Substance I designation | Function | Concentration/dose in wt. % |
|---|---|---|
| Beta interferon | Active ingredient | 0.1 μg to 200 μg per MNA |
| Polyvinylpyrrolidone (PVP) | Adjuvant | 0.1% to 95% (m/m) |
| Trehalose | Adjuvant | 0.1% to 45% (m/m) or up to 95% (m/m) |
| Polysorbate | Adjuvant | 0.001% to 10% (m/m) |
| Glycerol | Adjuvant | 0.1% to 10% (m/m) |
| Acetate buffer | Solvent | 0.01% to 10% (m/m) |

After the liquid formulation has been dried, for example to form a microneedle array (MNA) having a residual water content of 0.1 to 20% (m/m), a composition of the MNA is obtained that is changed accordingly by the loss of water.

The following examples and figures are provided to explain the invention in greater detail, without limiting the same.

EXAMPLES AND FIGURES

To produce the microneedles according to the invention, the known methods may be employed, such as McCrudden M T C, Alkilani A Z, McCrudden C M, McAlister E, McCarthy H O, Woolfson A D, et al. Design and physicochemical characterisation of novel dissolving polymeric microneedle arrays for transdermal delivery of high dose, low molecular weight drugs. J Control Release. 2014; 180: 71-80.

The above-described formulation was used within the scope of a preclinical in-vivo study (animal experiment model: Gottingen minipig).

FIG. 1 shows the active ingredient concentrations in the blood serum of the animals achieved after the delivery of the microarray.

Within the scope of the development of a clinical test apparatus for the beta interferon therapy, a dissolving microneedle or microarray patch (MNP) was produced and tested on the Gottingen minipig animal model.

The animal study confirms the successful use of the microarray, and the dissolution, absorption and distribution of the active ingredient substance in the animal experiment model. With this, the suitability of the active ingredient formulation was confirmed.

Even though the plasma concentration of beta interferon was lower intradermally than after SC injection, multiple sclerosis research experts are of the opinion that a higher potency could be achieved by directly releasing the active ingredient in the vicinity of the immunocompetent target cells in the upper layers of the skin. More importantly, according to experts, a lower active ingredient concentration could achieve a comparable treatment success, and considerably minimize the frequently occurring undesirable side effects. After a beta interferon injection (subcutaneous (SC) or intramuscular (IM)), the entire blood stream of the patient is usually flooded with a high concentration of cytokines within a very short time. This can be avoided with an intradermal application of the active ingredient since the active ingredient initially only reaches the interstitial liquid and the lymphatic system, and the corresponding potency, this being the initiation of immune cascades acting on the CNS, is triggered here.

Figure 2:
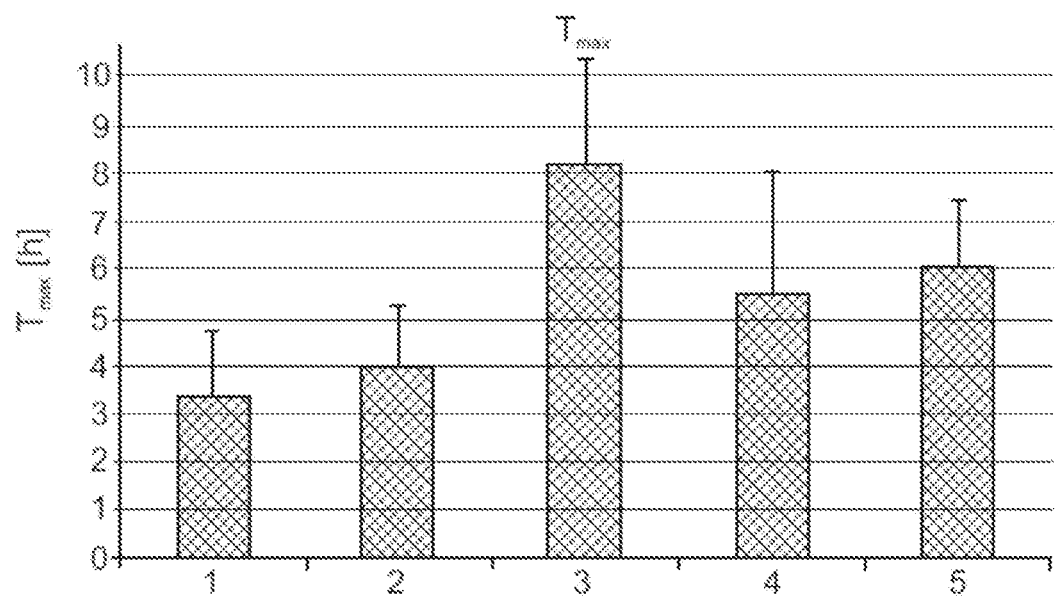

FIG. 2 shows the points in time until the peak plasma level of beta interferon is reached for the intradermal delivery by way of a microarray patch compared to the SC injection.

Figure 3:
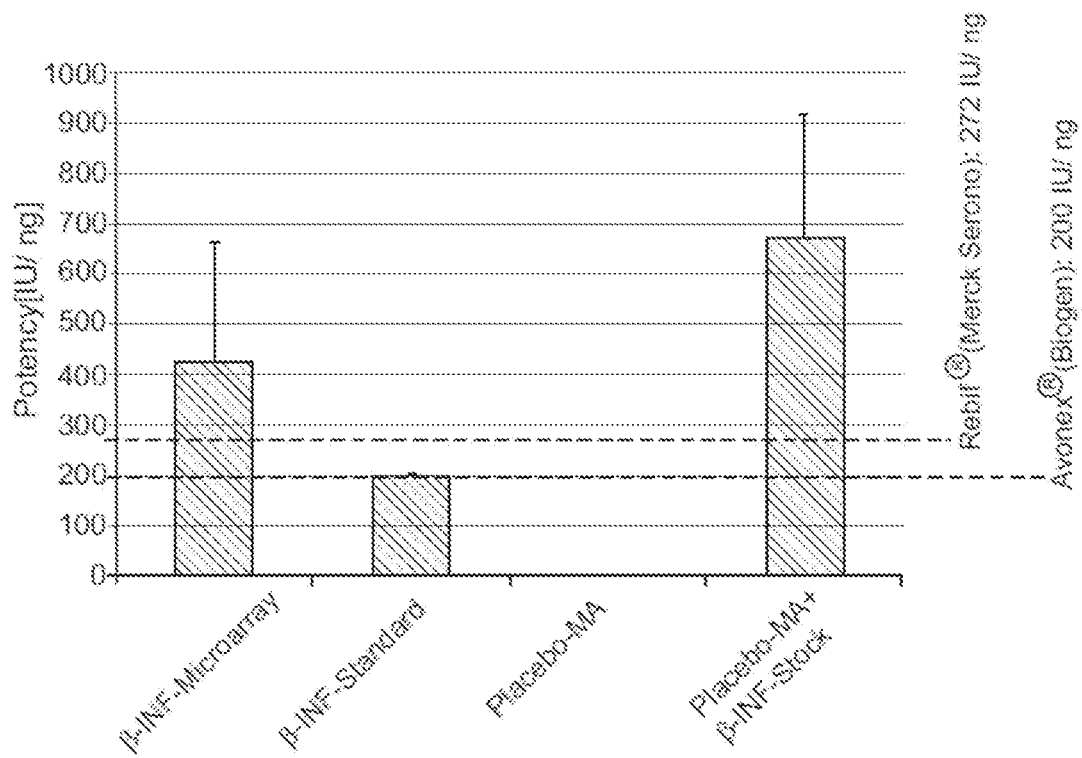

FIG. 3 shows an antiviral beta interferon activity assay including Hep-2C cells and infectious EMCV according to Ph. Eur. 5.2.3. The beta interferon microarray (MA) exhibits a higher activity, even though the amount is absolutely identical to the standard. The formulation of the beta interferon in a semi-solid form of administration of a microarray preserves the in-vitro activity.

As a result of the elimination of stabilizers and other adjuvants in the product formulation, undesirable side effects can be precluded. Excellent stability of the active ingredient in the semi-solid, amorphous microarray structure was shown without the addition of frequently used stabilizers (such as mannitol, HSA or arginine) in the MA formulation. Moreover, stability analyses show that beta interferon formulated in microarrays can be stored at room temperature, and exhibits a specific activity comparable to other beta interferon products stored in a cool environment. It is therefore advantageously possible to store and transport beta interferon in the MA formulation without the use of a cold chain.

Figure 4:
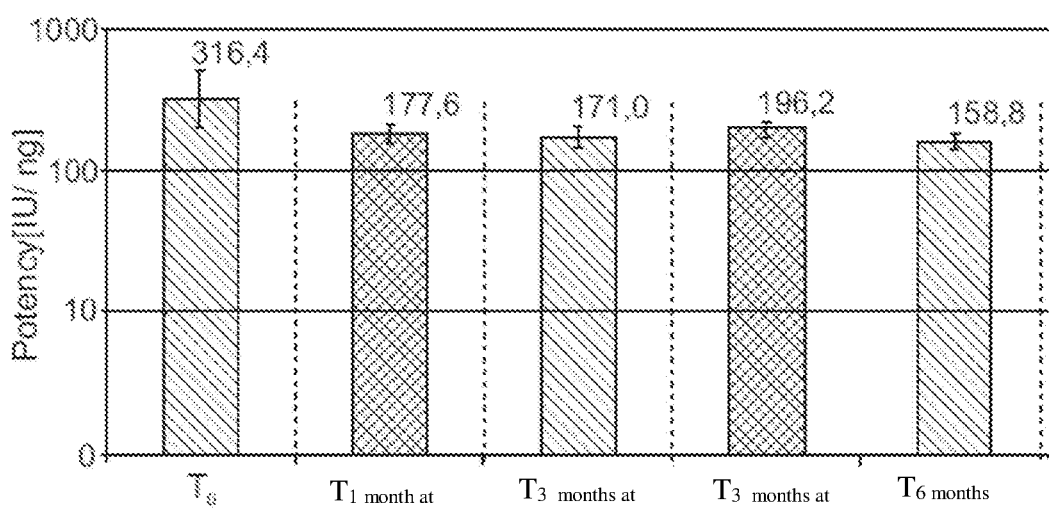

FIG. 4 shows the storage stability of the beta interferon microarray, and more particularly the in-vitro beta interferon activity analysis after production, after 1 month, 3 months, and after 6 months, while being stored at room temperature (21° C.) and at refrigerator temperature (5° C.). The antiviral potency of the beta interferon remains in the same log unit range as at the time of production, even after 6 months and a storage temperature of 21° C.

LEGEND FOR THE FIGURES

FIG. 1:

Averaged active ingredient concentration in the blood serum after the delivery of the microarray.

FIG. 2:

Points in time until the peak plasma level of beta interferon is reached for the intradermal delivery by way of a microarray patch compared to the SC injection.

Legend: 1 B-IFN-MA 100 g, 2 B-IFN-MA 200 g, 3 Drug substance 40 g SC., 4 Avonex 30 g S.C., 5 Rebif 44 g S.C.

FIG. 3:

Antiviral beta interferon activity assay including Hep-2C cells and infectious EMCV according to Ph. Eur. 5.2.3. Beta interferon microarray (B-IFN-MA) exhibits a higher activity, even though the amount is absolutely identical to the standard. The formulation of the beta interferon in a semi-solid form of administration of a microarray preserves the in-vitro activity.

FIG. 4:

Storage stability of the beta interferon microarray. In-vitro beta interferon activity analysis after production, after 1 month, 3 months, and after 6 months, while being stored at room temperature (21° C.) and refrigerator temperature (5° C.). The antiviral potency of the 316.4, 177.6, 171.0, 196.2, 158.8 [IU/ng] beta interferon remains in the same log unit range as at the time of production, even after 6 months and a storage temperature of 21° C.

The invention claimed is:

1. A microneedle array comprising interferon and a completely soluble formulation and the formulation comprises
- more than 35 wt % of polyvinylpyrrolidone with polyvinylpyrrolidone being present in the formulation in the greatest amount compared to the other ingredients,
- more than 25 wt. % of disaccharide,
- non-ionic surfactants, and
- polyalcohol.

2. The microneedle array according to claim 1, wherein the polyalcohol is glycerin, the disaccharide is trehalose, and the surfactant is polysorbate.

3. The microneedle array according to claim 1, characterized in that polyvinylpyrrolidone accounts for more than 45 wt. % in the formulation.

4. The microneedle array according to claim 1, wherein the interferon content is 10 μg to 100 μg per microneedle array.

5. A product comprising the microneedle array according to claim 1.

6. A pharmaceutical product comprising the microneedle array according to claim 1.

7. The microneedle array or according to claim 1, wherein the formulation comprises more than 35 wt % polyvinylpyrrolidone and further adjuvants and additives.

8. The microneedle array or according to claim 1, wherein the formulation comprises more than 35 wt % polyvinylpyrrolidone and the disaccharide is trehalose which is in an amount from more than 25 wt. % to 45 wt. %.

9. The microneedle array according to claim 8, wherein the surfactant is polysorbate which is in an amount from 0.001 wt. % to 10 wt. % and the polyalcohol is glycerin which is in an amount from 0.1 wt. % to 10 wt. %.

10. The microneedle array according to claim 9, which further comprises a solvent.

11. The microneedle array according to claim 10, wherein the solvent is an acetate buffer.

12. The microneedle array according to claim 11, wherein the interferon is beta interferon.

13. The microneedle array or according to claim 1, wherein the formulation comprises more than 35 wt % polyvinylpyrrolidone and the surfactant is polysorbate which is in an amount from 0.001 wt. % to 10 wt. %.

14. The microneedle array or according to claim 1, wherein the formulation comprises more than 35 wt % polyvinylpyrrolidone and the polyalcohol is glycerin which is in an amount from 0.1 wt. % to 10 wt. %.

15. A microneedle system comprising a microneedle array according to claim 1, and an applicator.

16. A microneedle system comprising a microneedle array and an applicator according to claim 15, wherein the applicator comprises a trigger device.

17. The microneedle array according to claim 1, wherein the disaccharide is trehalose which is in an amount from more than 35 wt. % to 45 wt. %.

18. The microneedle array according to claim 1, wherein the disaccharide is trehalose which is in an amount from more than 35 wt. % to 45 wt. % and the polyvinylpyrrolidone is in an amount of at least 55 wt. %.

19. The microneedle array according to claim 1, which further comprises a solvent.

20. The microneedle array according to claim 8, wherein the solvent is an acetate buffer.

21. A microneedle array comprising a completely soluble formulation- and the formulation comprises
   interferon,
   more than 35 wt % of polyvinylpyrrolidone with polyvinylpyrolidone being present in the formulation in the greatest amount compared to the other ingredients,
   more than 25 wt. % of disaccharide,
   non-ionic surfactants, and
   polyalcohol.

* * * * *